United States Patent [19]

McMullen

[11] 4,437,815

[45] Mar. 20, 1984

[54] PUMP, AND AN APPARATUS INCORPORATING THE PUMP FOR INFUSING LIQUID MEDICINE

[76] Inventor: John K. McMullen, "Carragh" 11 Mount Aboo Park, Finahgy, Belfast BT10 ODJ, Northern Ireland

[21] Appl. No.: 269,042

[22] PCT Filed: Sep. 29, 1980

[86] PCT No.: PCT/GB80/00150

§ 371 Date: May 15, 1981

§ 102(e) Date: May 15, 1981

[87] PCT Pub. No.: WO81/00888

PCT Pub. Date: Apr. 2, 1981

[30] Foreign Application Priority Data

Sep. 27, 1979 [GB] United Kingdom ............... 7933486

[51] Int. Cl.³ ............................................. F04B 17/04
[52] U.S. Cl. ........................................ 417/418; 3/1.7; 251/65; 417/505; 604/152
[58] Field of Search ............... 128/DIG. 12, 214 F, 128/DIG. 3, 273; 417/505, 12, 417, 418, 538; 251/65, 139, 129; 137/528; 91/DIG. 4; 3/1.7; 604/151, 152

[56] References Cited

U.S. PATENT DOCUMENTS

| | | | |
|---|---|---|---|
| 2,597,952 | 5/1952 | Rosenlund | 251/65 X |
| 2,925,814 | 2/1960 | Vibber et al. | 128/214 F |
| 2,962,593 | 11/1960 | Thomas | 251/65 X |
| 3,205,787 | 9/1965 | Volkmann | 91/DIG. 4 |
| 3,437,044 | 4/1969 | Sanders et al. | 417/418 |
| 3,874,822 | 4/1975 | Nakamura | 417/505 X |
| 4,159,026 | 6/1979 | Williamson | 251/65 X |
| 4,274,407 | 6/1981 | Scarlett | 128/214 F X |

Primary Examiner—Edward K. Look
Attorney, Agent, or Firm—Gerald J. Ferguson, Jr.; Joseph J. Baker

[57] ABSTRACT

The pump has a chamber in which a piston reciprocates to pump a liquid. The piston is moved by having secured thereto the armature of at least one electromagnet (preferably two). The coil of the electromagnet is suitably external of the pump casing. A control circuit pulses the electromagnet at a predetermined rate to provide a predetermined periodic output.

In a preferred form, the pump is mounted together with a liquid reservoir on a printed circuit board, and the unit is encapsulated for implantation in the human body to infuse a liquid medicine at a controlled rate into the bloodstream.

6 Claims, 7 Drawing Figures

PUMP, AND AN APPARATUS INCORPORATING THE PUMP FOR INFUSING LIQUID MEDICINE

This invention relates to a pump and to an apparatus incorporating such a pump for infusing into a subject determined quantities of liquid medicine at pre-determined time intervals.

The invention has particular, but not exclusive, relevance to medical applications in which controlled doses of drugs must be administered over long periods of time. For instance, persons suffering from diabetes melitus require routine administration of insulin, which is normally given by self-injection. Not only does this raise problems of maintaining supplies of sterile needles and the like, but the use of injections tends to limit administration to once or twice daily, and the resulting concentration of insulin in the blood fluctuates widely.

In this and other applications, there is a need for a means of infusing drugs at a controlled rate so as to give relatively small amounts at relatively frequent intervals, say one to four times per hour. Such frequency would preclude conventional injection.

Objects of the invention is therefore to provide a pump suitable for use in such infusion, and an infusion apparatus incorporating the pump.

According to the first aspect of the present invention, I provide a pump comprising a casing defining an elongate chamber, inlet and outlet valves communicating with the chamber, a piston coaxially movable in the chamber, and an electromagnet controlling movement of the piston via an armature, the outlet valve also being controlled by the electromagnet via a valve armature; characterised in that the inlet and outlet valves are balls made from a material having ferromagnetic properties and seats made of non-magnetic material and magnets tensioning the balls of said inlet and outlet valves against their seats when in a closed position, and in that power means for opening said balls from their seats, comprise for said inlet valve a force equivalent to a hydraulic force caused by coaxial movement of the piston in the chamber, said piston and said outlet valve being operated against the flow of liquid by the excitation of the single electromagnet, a piston lock magnet providing a biasing force on the piston thereby to inhibit unintentional movement of the piston, and said outlet valve remaining closed in response to adverse inlet or outlet pressure conditions to prevent inadvertent flow of liquid.

According to a second aspect of the present invention, I provide an apparatus for infusing into a subject determined quantities of liquid medicine at pre-determined time intervals, the apparatus comprising a pump in accordance with the preceding paragraph in combination with a reservoir, the pump further including at least one non-return valve for passing liquid pumped from the reservoir to a cannula for infusing the liquid into a subject, and the circuitry including timing means for actuating the piston at predetermined regular intervals.

Preferably, two electromagnet coils are wound around the casing of the pump.

Preferably also, the apparatus together with the cannula are implantable into the living tissue or cavities of the subject.

An embodiment of the present invention will now be described, by way of example, with reference to the accompanying drawings, in which.

Figure 2:
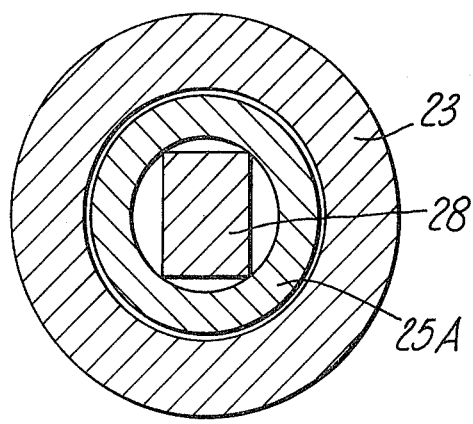
FIGS. 2 to 5 are respectively cross-sectional views of the pump along the lines II—II, III—III, IV—IV and V—V of FIG. 1, the views being to the same scale which is larger than that in FIG. 1.
Figure 3:
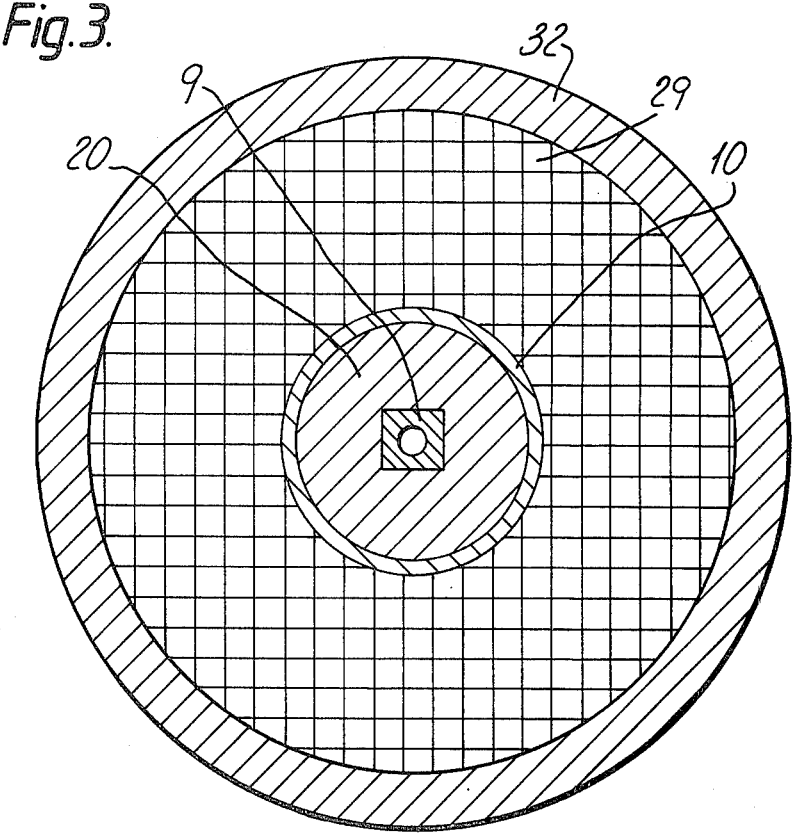
Figure 4:
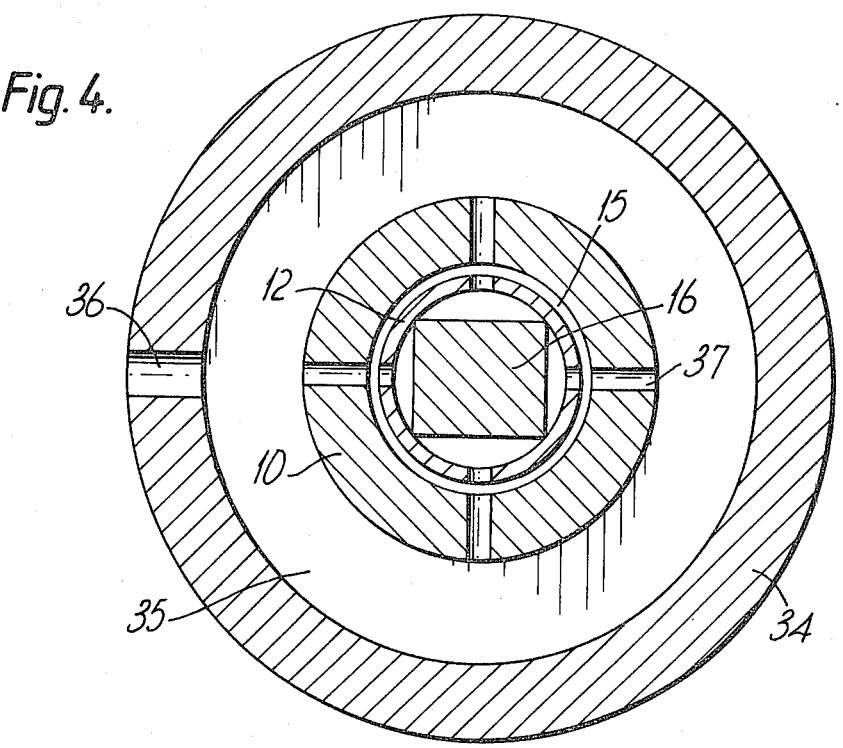
Figure 5:
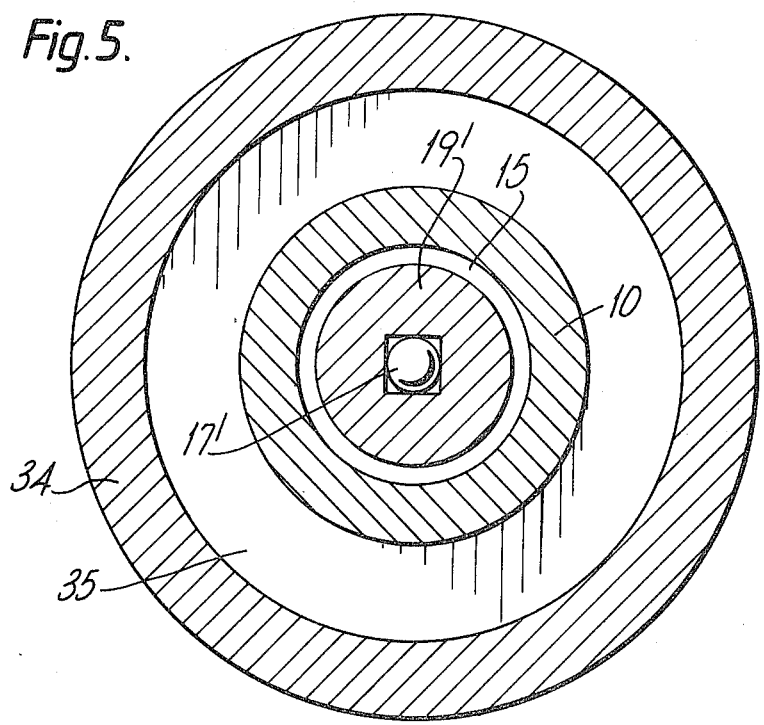

Referring to FIGS. 1 to 5 of the drawings, a pump comprises a cylindrical casing 10 whose interior defines an elongate chamber 11. A piston 12 is co-axially movable in said chamber 11. The piston 12 is an assembly comprising a tube 12A which has on its outside circumference two similar rings 14 integral therewith and spaced apart on and proud of its surface. Each ring 14 is adjacent to an end of the piston 12. The lands on the outside of the rings 14 are in sliding engagement with the inside walls of the casing 10. Between the rings 14, piston circumference and the inside wall of the casing 10, an annular passage 15 is defined. Mid-way of the bore 8 of the tube 12A a square inlet valve magnet 16 is in push-fitted engagement (FIG. 4). Symmetrical about the magnet 16, two similar inlet valves are provided comprising balls 17,17' and seats 18,18'. An axially-bored plug 19,19' secures the balls 17,17' and seats 18,18' in their positions in the piston. To the outside end wall of the plugs 19,19', a piston armature 20,20' is secured. The armatures 20,20' are bored in axial alignment with the bores in the plugs 19,19' and are both co-axial with the tube 12A and casing 10. Piston lock magnets 9,9' are mounted in axial recesses in outer end walls of piston armatures 20,20'.

Figure 1:
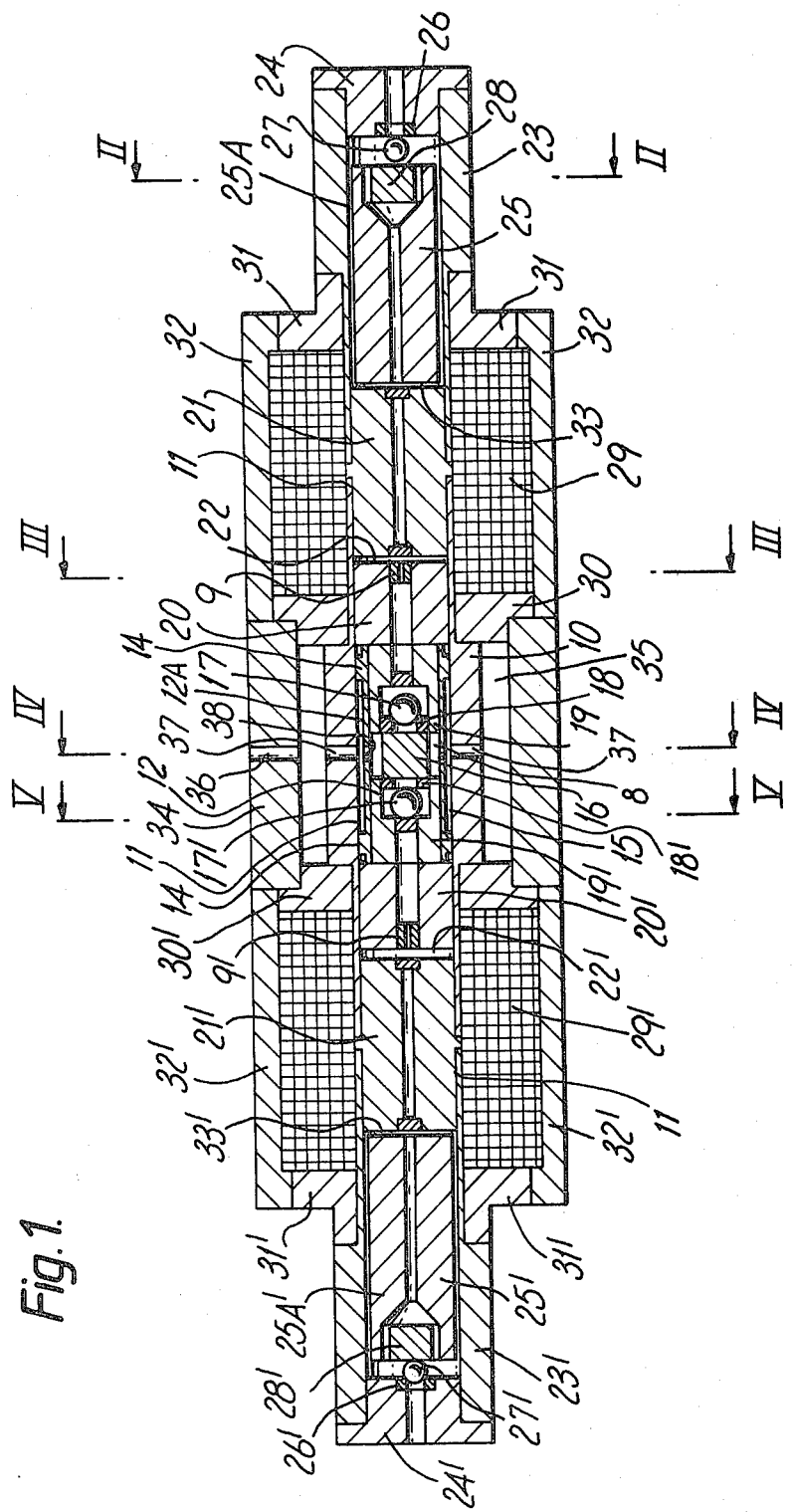
FIG. 1 is a lengthwise cross-section of a pump according to the present invention.

Two fixed cores 21, 21' are symmetrically secured in the opposite ends of the casing 10 leaving air gaps 22, 22' thereby to define the extent of reciprocal movement of the piston 12. Two similar sleeves 23, 23' are secured around the fixed cores 21, 21' as extensions of the casing 10. The outer ends of the sleeves 23, 23' are closed off by outlet valve plugs 24, 24' having axial bores. In the sleeves 23, 23' between the fixed cores 21, 21' and plugs 24, 24' two valve armatures 25, 25' are slidably movable. The armatures 25, 25' are formed from two materials to be defined hereinafter secured together the outer parts being 25A, 25A'. Two similar outlet valves are provided comprising balls 27, 27' and outlet valve seats 26, 26'. The seats 26, 26' are located in axial recesses and the inner end of plugs 24, 24'. Square outlet valve magnets 28, 28' are provided in cylindrical recesses in the outer ends of valve armatures 25, 25' (FIG. 2). Two electromagnet coils 29, 29' are provided wound respectively around the fixed cores 21, 21' as shown in FIGS. 1 and 3 and between collars 30, 30' and 31, 31' and covers 32, 32' are provided to fit over the outside of the coils 29, 29'. Valve air gaps 33, 33' are provided between fixed cores 21, 21' and valve armatures 25, 25'.

An annulus 34 is provided around the pump casing 10 and seats in collars 30, 30' and an annular passage 35 is defined between said annulus 34 and casing 10. Annulus 34 has a port 36 to be secured to a reservoir of fluid, the port 36 communicating with passage 35. Casing 10 has four equi-spaced ports 37 allowing fluid communication from passage 35 to passage 15, and tube 12A has four equi-spaced ports 38 allowing fluid communication from passage 15 to bore 8.

Annulus 34, sleeves 23, 23', casing 10, plugs 19, 19' and ports 25A, 25A' of valve armatures 25, 25' are all of non-magnetic material such an Inionel 600, but can be of non-magnetic stainless steels or plastics. The iron path comprises of the collars 30, 30'; 31, 31' and cover 32, 32', together with the fixed core 21, 21', the valve armature 25, 25' except parts 25A, 25A' referred to above, and the piston armatures 20, 20' are all of a material such as Mu-metal, although other materials for example Mu-metal plus, Super Mu-metal, Ortho metal, Super Radio metal or Permendor can be used.

The balls 27, 27' and 17, 17' are of Tungsten Carbide, although they could be of a material such as those used above for the fixed cores 21, 21'. The valve seats 26, 26' and 18, 18' are of synthetic sapphire but can be of ceramics, Inconel 600, non-magnetic stainless steels or plastics. The magnets 16, 9, 9' and 28, 28' are all of sintered cobalt-samarium but can be of Alnico, platinum cobalt, nialco, reco, conife, or cumico.

Pumping action is achieved by alternately energising the coils 29, 29' of the electromagnets to achieve reciprocation of the piston 12. Induction of fluid is achieved by the two inlet valves whose motion is controlled by the hydraulic forces generated by the motion of the piston 12. The outlet valves are powered open by electromagnet means. This is achieved by having the fixed core 21, 21' to act as a stop in each electromagnet and using a second armature 25, 25' to pull the outlet valve open as the piston is pulled into the electromagnet.

With reference to FIG. 1, the electromagnet coil 29 is energised causing magnetic flux to set up around the iron path comprised of the collar 30, collar 31 and cover 32, and thus through the valve armature 25, fixed core 21, and piston armature 20. This causes the piston armature 20/piston 12 to abut against the fixed core 21 closing air gap 22 to exhaust a volume of liquid in said air gap equal to the volume of the air gap. The electric power to coil 29 is then switched off. By causing an electric current to flow in electromagnet coil 29', the air gap 22' will be closed to pump liquid. The piston 12 is held in its rest position by the piston locking magnets 9, 9' which are mounted in the piston armatures 20, 20'. This ensures that the piston 12 will not drift between strokes as a result of leaks in the valves or piston seals. In considering the inlet valve assemblies, each valve consists of a ball and seat. The ball has magnetic properties similar to iron and the seats are of non-magnetic material as mentioned above. The balls 17, 17', when the valves are not operating, are tensioned against their seats 18, 18' by the inlet valve magnet 16. In FIG. 1, the piston 12 has been pulled across by piston armature 20 being forced to close air gap 22 by a current flowing through electromagnet coil 29. This causes the air gap 22' to open creating a negative pressure which is transmitted through the axial bore in piston armature 20' and thence to the inlet ball 17'. This hydraulic force overcomes the magnetic force seating the ball 17' and causes fluid to flow from the reservoir through port 36 into passage 35 and through ports 37 into passage 15 and thence to fill air gap 22' by the fluid passages provided. Once the pressure is equalised then the ball 17' will seat under the influence of the magnetic force from the inlet valve magnet 16.

In considering the outlet valve assemblies, these comprise the valve armatures 25, 25'. The parts of the armatures to be under the influence of the solenoids are made from materials similar in magnetic properties to iron, the materials being given above. The part of the armature valves housing the outlet valve magnets 28, 28' are made from non-megnetic material, details of the materials being given above. This is to ensure the valve armatures 25, 25' are not held in the energised position by stray flux from the magnets 28, 28'.

It would be obvious to one with ordinary skill in the art that since the outlet valve balls 27, 27' are made from a material having ferromagnetic properties they will be attracted to the centre of the face of the outlet valve magnets 28, 28'. It is therefore apparent that they will be free to centralise in the non-magnetic outlet valve seats 26, 26'. The valves held in the closed position by the outlet valve magnets 28, 28' pulling against the outlet valve plugs 24, 24' which have ferro-magnetic properties. The closing force on the outlet valves greatly exceeds the closing force on the inlet valves ensuring that they are not moved by the hydraulic forces operating the inlet valves.

Outlet valve 27 operates as follows: Coil 29 is energised. Before the piston with piston armatures moves for piston armature 20 to abut fixed core 21 thereby closing air gap 22, piston armature 20' was against fixed core 21' and held there by the piston lock magnet 9'. This holding force is of the same order as the pull exerted on the valve armature 25 by the outlet valve magnet 28 on the outlet valve plug 24. These forces cancel each other out. The valve air gap 33 in its start position is less than the piston air gap 22 in its start position, thus the pull on the valve armature 25 will exceed that on the piston armature 20 ensuring the outlet valve 27 will open to allow fluid to be exhausted. Two hydraulic considerations also ensure that the valve will open. The first part of the force exerted on the piston armature 20 will be required to unseat the ball valve 17'. Secondly, the hydraulic pressure generated by closing air gap 22 will restrain the motion of the piston 12 by acting on the area bounded by the seal on the piston. The fluid has free passage around and through the valve armature 25 so the hydraulic force will be distributed on both faces of this component (less the small area where the ball contact the magnet). The sum of all these force considerations mean that the outlet valve will open. Outlet valve 27' operates in a similar manner on coil 29' being energised.

The fact that the valves in the pump operate on the same current pulse as the piston allows relatively simple driving circuits. The powering of the valves against the flow of liquid through the pump is a safeguard against inadvertent flow of liquid. For example, a rise of pressure at the outlet greater than the pressure which the pump will work into locks the inlet valve shut.

Similarly, a rise in reservoir pressure will lock the outlet valve when the hydrostatic force on the outlet valve ball overcomes the attractive force between this member and the outlet valve magnet.

Figure 6A:
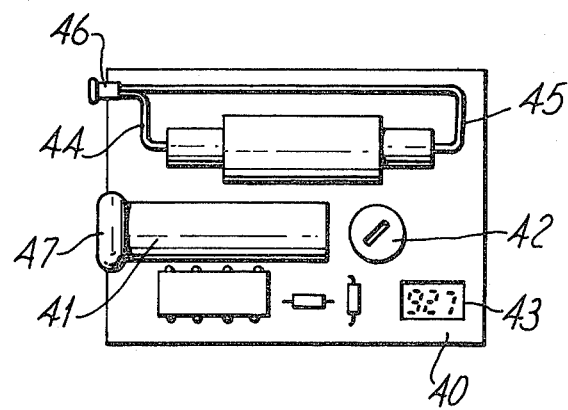
FIGS. 6A and 6B are respectively a plan view and an end view of an apparatus according to the present invention of a size implantable into the living tissue or cavities of a subject.
Figure 6B:
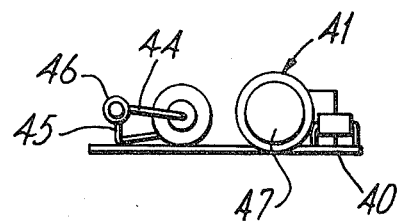

An apparatus for infusing into a subject, namely an animal or human being, determined quantities of liquid medicine at predetermined time intervals is shown in FIGS. 6A and 6B and comprises a printed circuit base board 40 having electronic components thereon, a pump as described above side-by-side with a reservoir 41, power means 42, a liquid crystal visual display unit 43, tubing 44 and 45 from both ends of the pump to an outlet 46 to be connected to a cannula (not shown). The reservoir has a self sealing bung 47 for injecting refil liquid medicine into the reservoir 41. The power means 42 are lithium batteries but may alternatively be atomic batteries. The apparatus as shown in the FIGS. 6A and 6B are actual size for implanting subcutaneously or for positioning in cavities in a human body. The apparatus may however be portable in the form of a watch to be strapped to the wrist.

Also, the apparatus may be of increased size and usable with existing drip-feed equipment.

The implantable and wrist strap models are primarily for administering liquid medicine such as insulin or heparin but can be used for infusing any liquid medicine while the human being is going about normal daily life.

The coils 29, 29' are of copper wire but for utmost efficiency with the smaller pumps may be of silver wire, the silver wire version giving on percentage increase in turns per equivalent copper wire version of 20%.

If the pump is to be frequently pulsed, then piston locking magnets 9, 9' could be omitted since there would not be time for leaks to occur.

The pump as described above can be modified without departing from the scope of the invention in the manner as follows:

(a) The passage 35 can be omitted.

(b) The inlet valve seats 18, 18' can be permanent magnets obviating the requirements for inlet valve magnet 18.

(c) The inlet valve balls 17, 17' can be permanent magnets and consequently the valve seats 18, 18' are of ferromagnetic or permanent magnetic material.

(d) The non-magnetic plugs 19, 19' can be of the same ferromagnetic material as the piston armatures 20, 20'. This will effect a holding force between the piston armature 20 or 20' and the fixed core 21 or 21' and so the piston locking magnets 9, 9' can be omitted.

(e) The outlet valve can have the fixed armature secured to its sleeve. In this case, if the sleeve had an outside diameter that fitted inside the piston armature bore then a screw-thread between them would allow the stroke of the pump to be altered.

(f) The pump can be single-acting instead of double-acting as above-described, in which case the pump will comprise one half of the pump described above i.e. as if it is cut along the line IV—IV and a plate of ferromagnetic material is used to effect a fluid seal. The inlet magnet will then provide a returning force when coil 29 was switched off. In this case, the coil 29 would need to provide more power.

The pump of the invention can be controlled by many forms of electronic control depending on use. For example when used as an implant it may form part of a closed loop system, controlled by a sensing device. An important feature of the pump is that it can easily be interfaced with a wide variety of electronics as it responds to intermittent pulsed information. Also, it has zero quiescent current consumption, the moving components having the magnets as "memories".

I claim:

1. A pump comprising a casing defining an elongate chamber, inlet and outlet valves communicating with the chamber, a piston coaxially movable in the chamber, and an electromagnet controlling movement of the piston via an armature, the outlet valve also being controlled by the electromagnet via a valve armature;

characterised in that the inlet and outlet valves are balls made from a material having ferromagnetic properties and seats made of non-magnetic material and magnets tensioning the balls of said inlet and outlet valves against their seats when in a closed position, and in that power means for opening said balls from their seats, comprise for said inlet valve a force equivalent to a hydraulic force caused by coaxial movement of the piston in the chamber, said piston and said outlet valve being operated against the flow of liquid by the excitation of the single electromagnet, a piston lock magnet providing a biasing force on the piston thereby to inhibit unintentional movement of the piston, and said outlet valve remaining closed in response to adverse inlet or outlet pressure conditions to prevent inadvertent flow of liquid.

2. A pump according to claim 1, in which a second electromagnet is spaced apart and axially aligned with the first electromagnet, the armatures of both electromagnets being oppositely linked together by the piston.

3. A pump according to claim 2, in which the electromagnets have coils wound around the casing.

4. A pump according to claim 3, in which those parts of the casing on which the coils are wound are relatively thin sleeves of non-magnetic material, and each coil is surrounded on its outer surfaces with relatively thick members of low-reluctance magnetic material.

5. An apparatus for infusing into a subject predetermined quantities of liquid medicine at predetermined time intervals, the apparatus comprising a pump in combination with a reservoir, the pump comprising a casing defining an elongate chamber, inlet and outlet valves communicating with the chamber, a piston coaxially movable in the chamber, and an electromagnet controlling movement of the piston via an armature, the outlet valve also being controlled by the electromagnet via a valve armature;

characterised in that the inlet and outlet valves are balls made from a material having ferromagnetic properties and seats made of non-magnetic material and magnets tensioning the balls of said inlet and outlet valves against their seats when in a closed position, and in that power means for opening said balls from their seats, comprise for said inlet valve a force equivalent to a hydraulic force caused by coaxial movement of the piston in the chamber, said piston and said outlet valve being operated against the flow of liquid by the excitation of the single electromagnet, a piston lock magnet providing a biasing force on the piston thereby to inhibit unintentional movement of the piston, and said outlet valve remaining closed in response to adverse inlet or outlet pressure conditions to prevent inadvertent flow of liquid, the pump having an outlet adapted to engage a cannula whereby liquid pumped from the reservoir may be infused into a subject, and including timing means arranged to actuate the piston at predetermined regular intervals.

6. An apparatus according to claim 5, in which the pump casing and the reservoir are mounted side-by-side on a printed circuit board which also carries control circuitry connected to the electromagnet.

* * * * *